United States Patent [19]
Smith et al.

[11] Patent Number: 5,721,143
[45] Date of Patent: Feb. 24, 1998

[54] SURFACTANT/DETERGENT TITRATION ANALYSIS METHOD AND APPARATUS FOR MACHINE WORKING FLUIDS, SURFACTANT-CONTAINING WASTEWATER AND THE LIKE

[75] Inventors: Douglas D. Smith, Knoxville; John M. Hiller, Oak Ridge, both of Tenn.

[73] Assignee: Lockheed Martin Energy Research Corporation, Oak Ridge, Tenn.

[21] Appl. No.: 823,152

[22] Filed: Mar. 25, 1997

[51] Int. Cl.$^6$ .................................................. G01N 31/16
[52] U.S. Cl. .................. 436/163; 422/75; 422/82.01; 422/82.09; 436/150; 436/164
[58] Field of Search .................................. 436/163, 164, 436/150; 422/68.1, 75, 82.01, 82.05, 82.09

[56] References Cited

U.S. PATENT DOCUMENTS

| | | |
|---|---|---|
| 3,969,076 | 7/1976 | Wang . |
| 3,989,661 | 11/1976 | Bondy . |
| 4,291,674 | 9/1981 | Comte et al. ............... 126/419 |
| 4,810,331 | 3/1989 | Garrison et al. .............. 204/1 T |
| 4,948,473 | 8/1990 | Phillippi .................. 204/153.2 |

OTHER PUBLICATIONS

Waters et al., Water Res. (1986), 20(2), 247–53.
Diaz et al., Collect. Czech. Chem. Commun. (1987), 52(3) 609–15.
Lukaszewski et al., TrAC, Trends Anal. Chem. (1996), 15(10), 525–531.
La Noce, Riv. Ital. Sostanze Grasse (1969), 46(12), 673–82.
Gian–Antonio Mazzocchin.G.Giogio Bombi and Guisseppe Alberto Sacchetto, Columetric Titrations with Iodide Ions in Molten (Li,K)NO$_3$, Electroanalytical Chemistry and Interfacial Electrochemistry, 1970, pp. 31–40.

Ferenc F. Gaal, Ljiljana S. Jovanovic and Velimir D. Canic, Biamperometric End–Point Determination in the Titration of Fluoride with Thorium Nitrate, Z. Anal. Chem., Band 272, Heft 2 (1974) pp. 117–120.

Primary Examiner—Jan Ludlow
Attorney, Agent, or Firm—J. Kenneth Davis

[57] ABSTRACT

The present invention is an improved method and related apparatus for quantitatively analyzing machine working fluids and other aqueous compositions such as wastewater which contain various mixtures of cationic, neutral, and/or anionic surfactants, soluble soaps, and the like. The method utilizes a single-phase, non-aqueous, reactive titration composition containing water insoluble bismuth nitrate dissolved in glycerol for the titration reactant. The chemical reaction of the bismuth ion and glycerol with the surfactant in the test solutions results in formation of micelles, changes in micelle size, and the formation of insoluble bismuth soaps. These soaps are quantified by physical and chemical changes in the aqueous test solution. Both classical potentiometric analysis and turbidity measurements have been used as sensing techniques to determine the quantity of surfactant present in test solutions. This method is amenable to the analysis of various types of new, in-use, dirty or decomposed surfactants and detergents. It is a quick and efficient method utilizing a single-phase reaction without needing a separate extraction from the aqueous solution. It is adaptable to automated control with simple and reliable sensing methods. The method is applicable to a variety of compositions with concentrations from about 1% to about 10% weight. It is also applicable to the analysis of waste water containing surfactants with appropriate pre-treatments for concentration.

13 Claims, 1 Drawing Sheet

SURFACTANT/DETERGENT TITRATION ANALYSIS METHOD AND APPARATUS FOR MACHINE WORKING FLUIDS, SURFACTANT-CONTAINING WASTEWATER AND THE LIKE

The United States Government has rights in this invention pursuant to contract no. DE-AC05-84OR21400 between the United States Department of Energy and Lockheed Martin Energy Systems, Inc.

FIELD OF THE INVENTION

The present invention relates to methods and apparatus for analyzing surfactant-containing aqueous streams, and more particularly to the analysis of machine working fluids.

BACKGROUND OF THE INVENTION

Machine working fluids provide lubricant and cooling properties for work piece/tool machining and other forming operations. Additional chemicals included in the composition function as metal scavengers, stabilizers, and biocides. These machine working fluids are usually proprietary compositions. Industrial machine working fluids contain surfactants and other chemical specie as variable mixtures and compositions which degrade with use and aging. A simple, reliable method of analysis for laboratory and on-line machine working surfactants and other compositions containing impure, degraded, and variable amounts of surfactants of different chemical forms in various amounts and stages of decomposition or oxidation is desired.

The American Society for Testing Materials offers several standard surfactant analytical methods. They in general are too complex, time-consuming, and require noxious chemicals for testing. Optical methods based strictly on the surfactant's index of refraction have been used, but degraded components and other materials such as dirt and particulate material in the machine working fluids limit their use. Typically, extraction of the surfactant is a separate step, often by methylene chloride, carbon tetrachloride, or ethyl acetate which is used to separate the surfactant from the matrix. Mixtures of surfactants can be separated/analyzed by chromatography, spectroscopy, and polarography. They are primarily used for laboratory analytical methods.

Three major surfactant types are characterized as anion, cation, and neutral (nonionic and amphoteric) forms. Metal working fluids can and in some cases do use all three surfactant types in their compositions. Anion surfactant types include alkylbenzenesulfonates, alkyl sulfates, alkyl ether sulfates, alkane sulfonates, olefin sulfonates, pertoneum and lignin sulfonates, phosphate esters, and soaps, acetylated amono acids and sulfosuccinates.

Analysis of anionic surfactants is usually by Hyamine (Benzthonium chloride) cationic surfactant (potentiometric) using a surfactant selective electrode. Other methods include liquid and gas chromatography. Cationic surfactants include benzylalkyidimethylammonium salts, quaternary ammonium salts, amino acids, carboxybetaines, and phospholipids (lecithins). Cationic surfactants may be analyzed with anionic surfactant reagents. Quaternary amines can be titrated as an acid/base titration or with sodium dodceyl sulfate or sodium tetraphenylborate.

Titration of a cationic with only an anionic surfactant using turbidity as an indicator is described in the literature. It uses maximum turbidity as the equivalence point. Hendry, J. B. M., Read. Photometric Determination of Cationic Surfactants, *Analyst* 1988.113, 1249-51.

The method and apparatus of the present invention satisfy this need for on-line measurement capability. The method and apparatus are amenable to both laboratory and process analysis of machine working fluids and aqueous streams and streams that can be rendered aqueous which contain significant quantities of surfactants. A need exists to install low maintenance, reliable, on-line process analytical instrumentation for the analysis of surfactants in machine working fluids and other aqueous streams and streams that can be rendered aqueous in factories and other installations, especially where few large machine working fluid systems provide the capacity for many individual machines or stations. With the present invention, monitoring and analysis of the machine working fluid can be done quickly, efficiently, and accurately with automated equipment, using reagants and techniques that are environmentally safe and acceptable.

Alternatively, surfactants and detergents in waste water and other aqueous solutions can be analyzed by first extracting and/or concentrating the water sample surfactants by vacuum distillation or similar separation techniques well-known in water treatment plant operations. Discharge water must be analyzed for surfactants to satisfy laws and regulations. In another alternative, this invention could be used to monitor surfactants in air or other gases. Recently the regulations regarding aerosols have lowered the limits by a factor of 10. Thus surfactants in breathing air may be monitored by first rendering them aqueous by methods well known to the skilled artisan. The method may also provide information on the biodegradability of the compositions or enhance biodegradible reactions. The spent analysis product solution does not contain significant amounts of chemicals regulated by the Resource Conservation and Control Act (RCRA) and the like.

The method and apparatus of this invention minimize problems of detergent on-line analysis in compositions containing variable dirty, aged, or decomposed components such as machine working fluids. The titration method uses a soap reaction, the products of which are relatively insoluble in the titration matrix solution and are removed from the solution by co-precipitation with the bismuth or other highly charged ion soap which is generated in the titration reaction. The reaction is shown to be detectible by several means including electrometric (potentiometry by surfactant electrode) and physical (turbidimetric) means to a variety of anion, cation, and neutral surfactant/detergent specie.

OBJECTS OF THE INVENTION

Accordingly, it is an object of the present invention to provide a new and improved method for analyzing machine working fluids, surfactant-containing wastewater, and the like.

It is another object to provide a new and improved apparatus for analyzing machine working fluids, surfactant-containing wastewater, and the like.

Further and other objects of the present invention will become apparent from the description contained herein.

SUMMARY OF THE INVENTION

In accordance with one aspect of the present invention, the foregoing and other objects are achieved by a method for measuring the amount of surfactant in an aqueous fluid which comprises the steps of: providing a known-quantity test sample of the fluid; combining with the test sample a known quantity of titrant, the titrant comprising a known-concentration solution of bismuth nitrate in glycerol to produce a titration reaction, the titration reaction being continued at least to an end point, the titration reaction being characterized by at least one quantifiable change in parameter of the test sample, the change being selected from the group of changes consisting of physical changes, optical changes, thermal changes, and electrical changes; detecting the end point and controlling the quantity of titrant combined with the test sample so that the amount of titrant to achieve the end point of the titration reaction is known; quantifying the change in parameter, and; determining from the amount of titrant required to continue the titration reaction to its end point, and from the quantity in the change in parameter, the quantity of surfactant contained in the test sample of the aqueous fluid.

In accordance with a second aspect of the present invention, the foregoing and other objects are achieved by an apparatus for measuring the amount of surfactant in an aqueous fluid which comprises: means for obtaining a known quantity test sample of the fluid; a test chamber communicably connected to the means for obtaining a test sample; combining means for combining the test sample with a known quantity of titrant within the test chamber, the combining means capable of providing to the test chamber a known concentration solution of bismuth nitrate in glycerol, to produce a titration reaction, the titration reaction being continued at least to an end point, the titration reaction being characterized by at least one quantifiable change in parameter of the test sample, the change being selected from the group of changes consisting of physical changes, optical changes, thermal changes, and electrical changes, the combining means being communicably connected to the test chamber; detection means for detecting the end point, the detection means operably connected to said combining means to control the quantity of titrant that is combined with the test sample so that the amount of titratant to achieve the end point of the titration reaction is known; quantifying means for quantifying the change in parameter, the quantifying means being operably disposed to permit quantifying the change in parameter, and; calculating means for determining from the amount of titrant required to continue the titration reaction to its end point, and from the quantity in the change in parameter, the quantity of surfactant contained in the test sample of the aqueous fluid, the calculating means being operably connected to the other means of the apparatus.

BRIEF DESCRIPTION OF THE DRAWING

FIG. 1 is a schematic showing one embodiment of an apparatus for measuring the amount of surfactant in a machine working fluid 1 in a continuous or on-line mode of operation comprises a means for repetitively extracting a sample of a machine working fluid 10, a means for injecting the sample of machine working fluid into a test cell means 11; a test cell means 11 of sufficient size and being capable of being used in the discrete sample operation with stirring of the test solution and titrant; an injection means 12 for injecting a known quantity of bismuth nitrate/glycerol or other reactive composition into the test cell means at a selectable, variable, and repetitive rate; a determination means (sensor) 13 for determining the change in a physical, optical, or electrical parameter in the test cell caused by the introduction and subsequent reaction of the bismuth nitrate/glycerol solution with the machine working fluid surfactant components; a calculating means 14 for calculating the end or transition point of the titration reaction based on sensor data values generated by the repetitive injection of the titrant; a stopping means 15 for stopping the titrant test operation, draining and removing the spent solution to another volume for storage or discarding; a cleaning means 16 for rinsing or cleaning the test cell means in preparation for the subsequent test; and a processor means 17 for repetitively determining and controlling the state, operation, and function of all the other means of the test apparatus.

Figure 1:
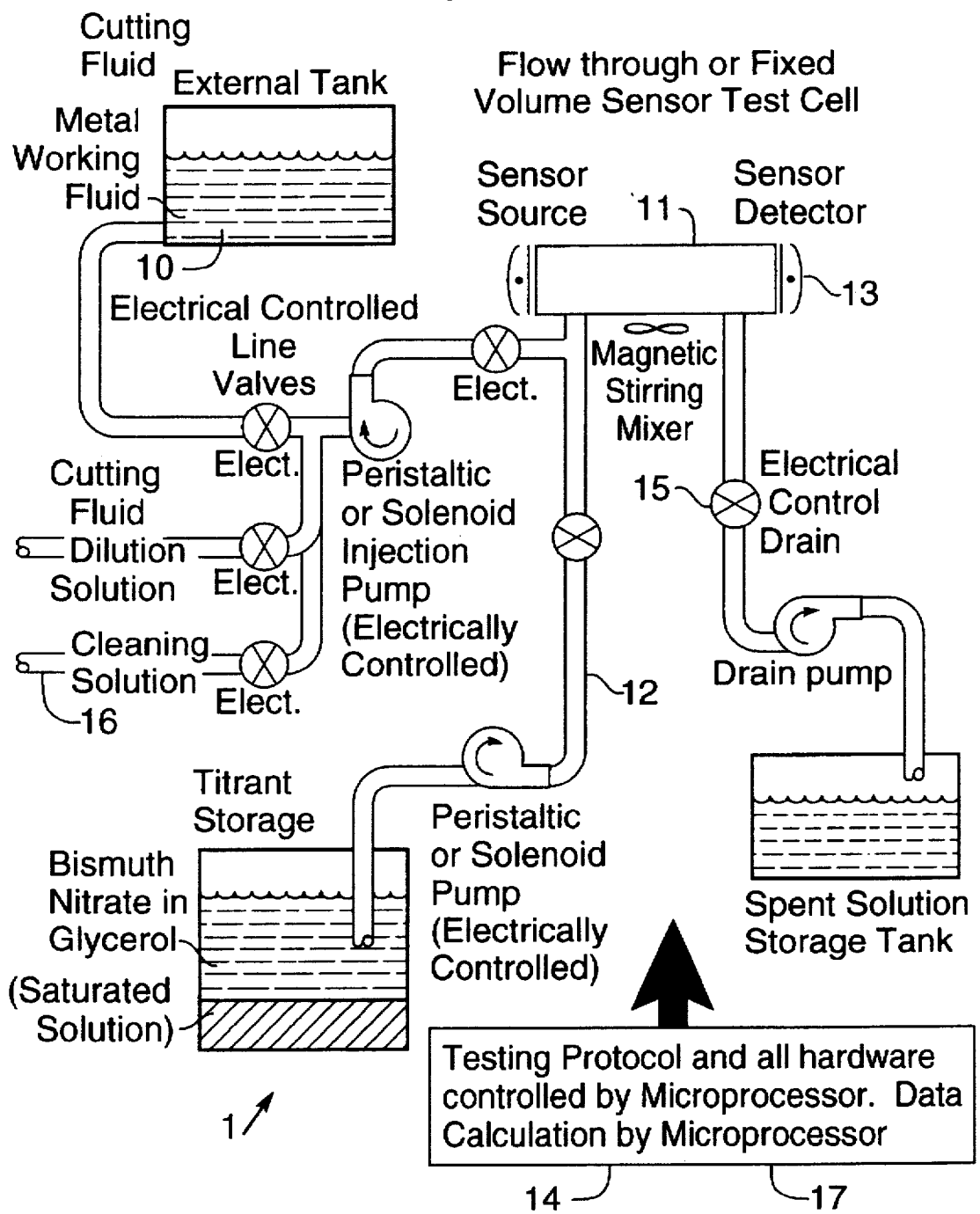
FIG. 1 shows an apparatus for the practice of the instant invention.

For a better understanding of the present invention, together with other and further objects, advantages and capabilities thereof, reference is made to the following disclosure and appended claims in connection with the above-described drawings.

DETAILED DESCRIPTION OF THE INVENTION

Herein is described an improved, general-purpose method and apparatus for the quantitative analysis of several types of machine working fluids and other aqueous compositions containing various mixtures of cationic, neutral, and/or anionic surfactants, soluble soaps, and other chemical specie. The present invention is a reactive titration method and apparatus based on the solubility of bismuth nitrate dissolved in glycerol and its reaction with surfactant specie to form micellar variations, suspensions, or insoluble curds or soaps with the surfactant in the machine working fluid. The method uses a single phase, non-aqueous, reactive titration composition comprising water insoluble bismuth nitrate dissolved in glycerol for the titration reactant or titrant. The chemical reaction of the bismuth ion and glycerol with the surfactant in the test solution yields formation of micelles, changes in micelle size, and the formation of insoluble bismuth soaps. These insoluble bismuth soaps are quantified by measurements of the physical and/or chemical changes in the aqueous test solution due to the titration reaction. Both classical potentiometric analysis and turbidity measurements have been used as sensing techniques to determine the quantity of insoluble bismuth soaps in the reacted test solutions, and thus to indicate the quantity or concentration of surfactant present in the test solution prior to the reaction. Other sensing techniques known to the skilled artisan may be used as well. The method is amenable to the analysis of several types of in-use, aged, dirty, and decomposed surfactant and detergent solutions, as well as new surfactant and detergent solutions. It is a quick and efficient process using the single-phase reaction method without requiring a separate extraction from the aqueous solution. The process uses non-toxic chemicals. It is adaptable to automated control with simple and reliable sensing methods. The invention is applicable to both bench and on-line applications with a variety of compositions, especially metal working fluids having surfactant concentrations between about 1 and about 10% weight, and to analysis of waste water containing lesser concentrations of surfactants with appropriate sample pre-treatments for increasing surfactant concentration. A schematic adaption to on-line instrumentation for continuous, analytical process use is shown in FIG. 1.

Several hundred experiments including a machine working fluid challenge suite of samples have been conducted using the method to prove its general utility. Used unknown machine working fluid residue taken from the pan of an out-of-service lathe was also tested with successful results. Detection of the titration endpoint/transition is either by a chemical or physical method. In one embodiment, shown in FIG. 1, an apparatus for measuring the amount of surfactant in a machine working fluid 1 in a continuous or on-line mode of operation comprises a means for repetitively extracting a sample of a machine working fluid 10, a means for injecting the sample of machine working fluid into a test cell means 11; a test cell means 11 of sufficient size and being capable of being used in the discrete sample operation with stirring of the test solution and titrant; an injection means 12 for injecting a known quantity of bismuth nitrate/glycerol or other reactive composition into the test cell means at a selectable, variable, and repetitive rate; a determination means (sensor) 13 for determining the change in a physical, optical, or electrical parameter in the test cell caused by the introduction and subsequent reaction of the bismuth nitrate/glycerol solution with the machine working fluid surfactant components; a calculating means 14 for calculating the end or transition point of the titration reaction based on sensor data values generated by the repetitive injection of the titrant; a stopping means 15 for stopping the titrant test operation, draining and removing the spent solution to another volume for storage or discarding; a cleaning means 16 for rinsing or cleaning the test cell means in preparation for the subsequent test; and a processor means 17 for repetitively determining and controlling the state, operation, and function of all the other means of the test apparatus.

The cleaning means may further comprise other hardware items such as line valves, control valves, solenoids, injectors, peristaltic pumps, rinse pumps, and/or other means of cleaning the cell of insoluble soaps and other materials.

The calculating means may be a microprocessor for calculating the amount of surfactant present in the test sample based on a specified method of testing and data obtained from the test(s); or as a look-up table of stored data values and presenting them or generating a known signal based on this information.

For repetitive operation, a repeating means 17 for repeating the injection, testing, calculation, and cleaning operations and storing or transmitting the information generated from the test is desirable.

One alternative application for this method and apparatus includes monitoring cleaning processes such as laundering dirty or radioactively contaminated clothing or other articles, or other large-scale processes used in textile manufacturing. This method of analysis will allow the efficient use of cleaning detergents in process washing cycles. Soil contaminants such as PCBs or other organics may be removed using efficient detergents and surfactants in the washing/decontamination cycle.

A second alternative is analysis of process waste water or water treatment processes. These applications may require some sample pre-treatment such as vacuum distillation to increase the quantity and concentration of surfactant present depending on its amount and presence of other contaminants in the sample matrix. Analysis of surfactant in chemical manufacturing process operations to adapt to continuous rather than batch production analyses is possible. The method may be used to quantify a determination of sensitivity for decomposing surfactant solutions by biological means.

A third alternative is to use cations or chemical compounds other than bismuth and glycerol which form a general class of insoluble, non-toxic soaps other than the present composition.

A fourth alternative is to collect low levels of contaminant compounds containing lead, cadmium, mercury, nickel, chromium, or radioactive specie at collection electrodes using the passage of current to aid in the collection of insoluble soaps containing the desired specie to be removed from a matrix solution.

The present invention offers a number of unique features and advantages over the prior and related art. One advantage is that the titration method is applicable to a general and broad range of surfactant and detergent compositions and machine working fluids including cationic, anionic, and neutral forms of surfactants and detergents. It is amenable to measuring partially degraded, dirty, and decomposed compositions as are found in field use.

A second advantage is that this method is based on the use of a non-toxic and environmentally acceptable form of reaction using highly reactive bismuth (nitrate) ion in a soluble vehicle (media) of glycerol, water, and/or other chemical specie to provide the means of making an insoluble and benign reaction product which is easily detectable.

A third advantage is that the titration method does not normally require pre-concentration techniques for on-line or general machine working fluid analytical tests. However, pre-concentration can be achieved by such methods as vacuum condensation and the like if desired.

A fourth advantage is that partially used and degraded mixtures of several components of machine working fluid formulations can be tested with little or no sample preparation. The method is quick and reliable. Most of the insoluble metal grits, fines, soils, and other residues are removed in the precipitation process.

A fifth advantage is that the sensor means of titration reaction endpoints (e.g. turbidity units vs. mL bismuth nitrate/glycerol) have been demonstrated by turbidity measurement and potentiometric endpoints, (dE vs. mL bismuth nitrate/glycerol) for most of the surfactant compositions which have been tested.

A sixth advantage is that different methods of calculating the endpoints can be made depending on the type of test composition, the concentration of the bismuth nitrate/glycerol reactant or similarly functioning compositions and that of the machine working fluid.

A seventh advantage is that the concentration of the bismuth nitrate/glycerol reactant can be adjusted to accommodate specific conditions of measurement over large ranges with water or other liquids. A saturated solution of bismuth nitrate in glycerol can be diluted as needed for operation.

An eighth advantage is that the on-line version of the apparatus is simple and reliable in design and operation. A small microprocessor can control the needed valves and pumps to supply sample and reactant in needed quantities to a reaction mixing chamber. The chamber cleaning or rinsing means can also be easily set up. The titration method can be adapted to existing mixing/reaction schemes such as mechanical pulse modulation for fluid injection and sample test chamber cleaning methods. Small volume analysis waste solutions are less than (1. oz.) 25 cc/analysis. They can be disposed of by normal methods. Other measurement capability including temperature, pH, dissolved oxygen, and on-line turbidity can, if desired, be included in the measurement apparatus.

EXAMPLE I

Potentiometric titration of a metal working fluid composition employing a commercially available surfactant electrode (Orion Research Inc., Boston, Mass.; Model 93-42 Surfactant Cationic Anionic Sensing Electrode with reference electrode needed) was used. It sensed the change in the electrical potential of a fixed volume sample which was titrated with known amounts of reactive bismuth/glycerol solution. EMF data (mV) was recorded using an Orion Research, Inc., Boston, Mass., Expandable ionAnalyzer Model EA 640. The significant change in the electrical potential of the solution (usually an "S"-shaped curve of potential to the quantity of bismuth/glycerol added) after the addition of known amounts of titrant is the indicator of the reaction completion and thus the amount of surfactant present. Bismuth/glycerol titrant can be added by injection pipette or constant volume injection solenoid pipette or peristaltic pump to a constantly stirred (magnet bar) solution. The bismuth nitrate concentration range is 1.0 to 200 gms. per liter of glycerol. This solute is dissolved in the glycerol by ultrasonic means.

EXAMPLE II

Alternatively, and more adaptable to on-line measurement, the reaction equivalence point for the bismuth/glycerol titrant can be detected by nephelemetric (turbidimetric) means (light scattering/absorption properties of the machine working fluid changing to detect the transition endpoint). An HF Scientific, Inc. (Fort Meyers, Fla.) Model DRT-200B nephelometer (turbidimeter) with 28 mm path cuvette cell was used in the tests. For each single test of 25 mL of machine working fluid solution, turbidity output vs. amount of bismuth nitrate/glycerol added was recorded manually from a four digit Nephelometric Turbidity Units (1000 scale) display. The instrument also has flow-through cell measurement capability. Discrete injections (0.05 or 0.1 ml) of titrant were serially added to the test sample and turbidity data recorded for each addition after the reaction occurs. The transition end point is calculated by a calculation algorithm such as change in turbidity value. For any given test surfactant/concentration, a set of experiments using known quantities of surfactant mixtures are previously recorded for interpolation as "working curves". Interpolation and calculation of surfactant quantity present is easily accomplished by electronic calculation means.

While there has been shown and described what are at present considered the preferred embodiments of the invention, it will be obvious to those skilled in the art that various changes and modifications can be made therein without departing from the scope of the inventions defined by the appended claims.

What is claimed is:

1. A method for measuring the amount of surfactant in an aqueous fluid comprising the steps of:
   (A) providing a known-quantity test sample of the fluid;
   (B) combining with the test sample a quantity of titrant, said titrant comprising a known-concentration solution of bismuth nitrate in glycerol to produce a titration reaction, said titration reaction being continued at least to an end point, said titration reaction being characterized by at least one quantifiable change in parameter of the test sample, said change being selected from the group of changes consisting of physical changes, optical changes, thermal changes, and electrical changes;
   (C) detecting said end point and controlling and determining said quantity of titrant combined with said test sample so that the amount of titrant to achieve said end point of the titration reaction is known;
   (D) quantifying said at least one change in parameter, and;
   (E) determining from said amount of titrant required to continue said titration reaction to said end point, and from said quantified at least one change in parameter, the quantity of surfactant contained in the test sample of the aqueous fluid.

2. The method as described in claim 1 wherein the concentration of bismuth nitrate in glycerol is between about 1 gram bismuth nitrate per liter glycerol and about 200 grams bismuth nitrate per liter glycerol.

3. The method as described in claim 2 wherein the concentration of bismuth nitrate in glycerol is about 120 grams bismuth nitrate per liter glycerol.

4. The method as described in claim 1 wherein the at least one change in parameter is quantified using at least one method selected from the group of methods consisting of physical methods, optical methods, and electrical methods.

5. Apparatus for measuring the amount of surfactant in an aqueous fluid comprising:
   (A) means for obtaining a known quantity test sample of the fluid;
   (B) a test chamber communicably connected to said means for obtaining the test sample;
   (C) Combining means for combining the test sample with a quantity of titrant within said test chamber to produce a titration reaction, said combining means including a source of said titrant comprising a known concentration solution of bismuth nitrate in glycerol, the titration reaction being continued at least to an end point, the titration reaction being characterized by at least one quantifiable change in parameter of the test sample, the change being selected from the group of changes consisting of physical changes, optical changes, thermal changes, and electrical changes, said combining means being communicably connected to said test chamber;
   (D) Detection means for detecting the end point, said detection means operably connected to said combining means to control and determine the quantity of titrant that is combined with the test sample so that the amount of titratant to achieve the end point of the titration reaction is known;
   (E) Quantifying means for quantifying the at least one change in parameter, said quantifying means being operably disposed to permit quantifying the at least one change in parameter, and;
   (F) Calculating means for determining from the amount of titrant required to continue the titration reaction to its end point, and from the quantified at least one change in parameter, the quantity of surfactant contained in the test sample of the aqueous fluid, said calculating means being operably connected to the obtaining, combining, detecting and quantifying means.

6. The apparatus as described in claim 5 wherein the concentration of bismuth nitrate in glycerol is between about 1 gram bismuth nitrate per liter glycerol and about 200 gram bismuth nitrate per liter glycerol.

7. The apparatus as described in claim 6 wherein the concentration of bismuth nitrate in glycerol is about 120 grams bismuth nitrate per liter glycerol.

8. The apparatus as described in claim 5 wherein the at least one change in parameter is quantified using at least one method selected from the group of methods consisting of physical methods, optical methods, and electrical methods.

9. The apparatus as described in claim 5 further comprising means for stopping the titration reaction, draining and removing the titrated solution from the test chamber, said stopping means being operably connected to said test chamber.

10. The apparatus as described in claim 5 further comprising means for cleaning the test chamber in preparation for a subsequent test, said means for cleaning being operably connected to said test chamber.

11. The apparatus as described in claim 5 further comprising a processor means for repetitively controlling the obtaining, combining, detecting, quantifying and calculating means, said processor means being operably connected to the obtaining, combining, detecting, quantifying and calculating means.

12. The apparatus as described in claim 5 wherein the calculating means comprises a microprocessor.

13. The apparatus as described in claim 5 wherein the means for quantifying said change in said parameter comprises at least one of the group of means consisting of potentiometric means and turbidimetric means.

* * * * *

UNITED STATES PATENT AND TRADEMARK OFFICE
CERTIFICATE OF CORRECTION

PATENT NO. : 5,721,143
DATED : February 24, 1998
INVENTOR(S) : Douglas D. Smith and John M. Hiller It is certified that error appears in the above-identified patent and that said Letters Patent is hereby corrected as shown below:

On the Title Page, please correct the assignee's name as follows:

[75] "Assignee", please replace "Lockheed Martin Energy Research Corporation" with --Lockheed Martin Energy Systems, Inc.--.

Signed and Sealed this

Twentieth Day of July, 1999

Attest:

Q. TODD DICKINSON

Attesting Officer

Acting Commissioner of Patents and Trademarks